US011672697B2

(12) United States Patent
Gutierrez

(10) Patent No.: US 11,672,697 B2
(45) Date of Patent: Jun. 13, 2023

(54) EYE-MOUNTABLE THERAPEUTIC DEVICES, AND ASSOCIATED SYSTEMS AND METHODS

(71) Applicant: Twenty Twenty Therapeutics LLC, South San Francisco, CA (US)

(72) Inventor: Christian Gutierrez, San Francisco, CA (US)

(73) Assignee: TWENTY TWENTY THERAPEUTICS LLC, South San Francisco, CA (US)

(*) Notice: Subject to any disclaimer, the term of this patent is extended or adjusted under 35 U.S.C. 154(b) by 919 days.

(21) Appl. No.: 16/444,538

(22) Filed: Jun. 18, 2019

(65) Prior Publication Data

US 2019/0380871 A1 Dec. 19, 2019

Related U.S. Application Data

(60) Provisional application No. 62/686,780, filed on Jun. 19, 2018.

(51) Int. Cl.
*A61F 9/00* (2006.01)
*A61B 5/00* (2006.01)
(Continued)

(52) U.S. Cl.
CPC .............. *A61F 9/0017* (2013.01); *A61B 3/16* (2013.01); *A61B 5/4839* (2013.01);
(Continued)

(58) Field of Classification Search
CPC ...... A61F 9/0017; G16H 50/50; G16H 20/10; A61B 3/16; A61B 5/4839; A61B 5/4857; A61B 5/6821; A61B 5/7267; G02C 7/04
See application file for complete search history.

(56) References Cited

U.S. PATENT DOCUMENTS 6,939,299 B1 * 9/2005 Petersen ................ A61B 3/16
600/587
6,976,982 B2 12/2005 Santini, Jr. et al.
(Continued)

FOREIGN PATENT DOCUMENTS

WO  WO 2002067688    9/2002
WO  WO 2016/004262   1/2016
(Continued)

OTHER PUBLICATIONS

Hui, Alex, "Contact lenses for ophthalmic drug delivery," Invited Review, Sep. 2007, pp. 494-512, Clinical and Experimental Optometry 100.5, Australia.
(Continued)

*Primary Examiner* — Carl H Layno
*Assistant Examiner* — Aya Ziad Bakkar
(74) *Attorney, Agent, or Firm* — Tarolli, Sundheim, Covell & Tummino L.L.P.

(57) ABSTRACT

Systems, eye-mountable devices, and methods that facilitate chronotherapeutic treatment of primary open-angle glaucoma are provided which enable therapeutic products to be delivered to the eye in a controlled manner only when desired. According to one embodiment, an eye-mountable device comprises a substrate having an eye-mounting surface for positioning on an eye of a patient, a sensor that obtains a plurality of measurements representative of a condition of the eye of the patient over a period of time, a therapeutic agent delivery assembly coupled, and a processor for executing a temporal model of a therapeutic agent delivery in communication with the sensor and the therapeutic agent delivery assembly. The processor receives the plurality of measurements and activates the therapeutic agent delivery assembly to administer a first amount of a drug to the eye of the patient based on the temporal model associated with the plurality of measurements.

19 Claims, 10 Drawing Sheets

(51) Int. Cl.
    *G16H 20/10*     (2018.01)
    *A61B 3/16*     (2006.01)
    *G02C 11/00*     (2006.01)
    *G16H 50/50*     (2018.01)

(52) U.S. Cl.
    CPC .......... *A61B 5/4857* (2013.01); *A61B 5/6821* (2013.01); *A61B 5/7267* (2013.01); *G02C 11/10* (2013.01); *G16H 20/10* (2018.01); *G16H 50/50* (2018.01)

(56) References Cited

U.S. PATENT DOCUMENTS

| | | | |
|---|---|---|---|
| 9,289,123 B2 | 3/2016 | Weibel et al. | |
| 2009/0155338 A1 | 6/2009 | Conway et al. | |
| 2017/0258320 A1* | 9/2017 | Abreu | A61B 3/0025 |

FOREIGN PATENT DOCUMENTS

| | | | | |
|---|---|---|---|---|
| WO | WO-2017097708 A1 * | 6/2017 | ........... | A61N 5/0618 |
| WO | WO 2018/005891 | 1/2018 | | |

OTHER PUBLICATIONS

Glaucoma Research Foundation, "New Contact Lens Technology Could Change the Lives of Glaucoma Patients and Their Doctors," Blog news article, posted Nov. 18, 2016, 2 pages, https://www.glaucoma.org/news/blog/new-contact-lens-technology-could-change-the-lives-of-glaucoma-patients-and-their-doctors.php.

Hughes et al., "24-Hour Monitoring of Intraocular Pressure in Glaucoma Management: A Retrospective Review," article in Journal of Glaucoma vol. 12, No. 3, pp. 232-236, 2003, Lippincott Williams & Wilkins, Inc.

International Search Authority, International Search Report and Written Opinion, for PCT/US2019/037927, dated Oct. 4, 2019, 12 pages.

* cited by examiner

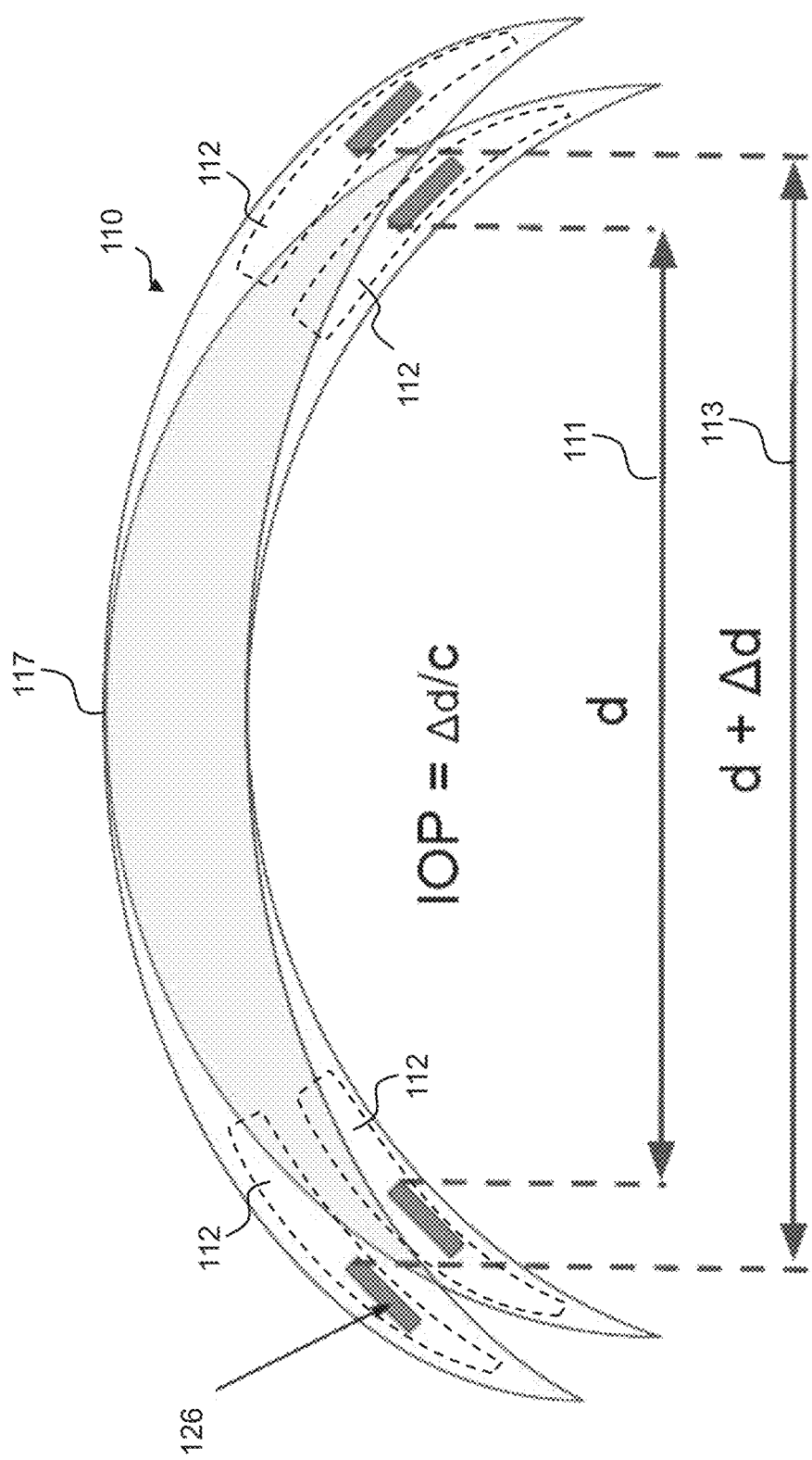

EYE-MOUNTABLE THERAPEUTIC DEVICES, AND ASSOCIATED SYSTEMS AND METHODS

CROSS-REFERENCE TO RELATED APPLICATIONS

The present application claims priority to and the benefit of U.S. Provisional Patent Application No. 62/686,780, filed Jun. 19, 2018, the entirety of which is hereby incorporated by reference.

TECHNICAL FIELD

The present disclosure relates generally to wearable physiological sensors and therapeutic devices, in particular, to eye-mountable sensors configured to obtain measurements of a physiological condition of the eye of a patient and administer a therapeutic agent based on the obtained measurements.

BACKGROUND

Diagnostic Primary open-angle glaucoma (POAG) is generally managed by reducing intraocular pressure (IOP) to a so called "target pressure." However, this pressure is difficult to identify because IOP fluctuates throughout the day in a 24-hour circadian cycle. Very little has been done to understand the consequences of these rhythms on the efficacy of pharmaceutical-based treatment paradigms. Dysregulation of IOP in glaucoma patients may extend beyond elevated pressures to also include differences in daily circadian cycles from normal subjects.

Clinicians initially believed that the level of IOP was highest in the morning, lower later in the afternoon and lowest at night. This belief has had clinical consequences: IOP has been measured only during the day, especially in the morning while the patient attended the clinical examination and treatment has therefore been developed to address this particular IOP profile, using drugs that inhibit the aqueous humour (AH) production, such as beta-blockers. Later, however, it was demonstrated that although in a significant number of glaucoma patients the 24-hour IOP values decrease during the night, in other normal subjects and patients with glaucoma the IOP curve had a different shape.

For example, FIG. 1 shows a graphical representation of intraocular pressure (IOP) measurements of a healthy patient and a patient affected by glaucoma. A first plot 12 represents the IOP measurements of the healthy patient over a period of approximately 24 hours, and a second plot 14 represents the IOP measurements of a patient affected by glaucoma over the same period. A circadian rhythm of both the healthy patient and the glaucoma patient can be observed as the relative increase in IOP during the "Sleep" period. During the "Wake" periods, that is, between approximately 6:30 a.m. and approximately 10:30 p.m., a difference between the IOP of the healthy patient and the IOP of the glaucoma patient increases. During the "Sleep" period, the difference between the IOP of the healthy patient and the IOP of the glaucoma patient decreases. The increase in IOP can be steep at the onset of sleep in young subjects and gradual, throughout the night in elderly. Moreover, night time IOP has been measured to be higher than daytime IOP in both young and elderly subjects. It has also been reported that glaucoma patients demonstrated a further increase in IOP between 5:30 and 7:30 in the morning, while normal subjects experienced a decrease in IOP. This understanding supports the conclusions that regulation of IOP in glaucoma patients was different from that seen in healthy subjects in more complex ways than just elevated pressure.

A variety of therapeutic approaches have been applied to treat and/or regulate IOP. To this day, the application of topical eye drops prescribed on a coarse schedule (e.g., mornings and/or evenings) has been the primary means of lowering IOP regardless of the stage of the disease. Patient-specific dosing schedules would be beneficial to better regulate IOP in glaucoma patients. However, the ability to execute precision drug delivery in patient-tailored therapeutic models presents a significant challenge given the well-documented patient non-compliance even with the simplest dosing schedules.

Thus, there remains a need for improved dosing regimens of therapeutic agents to manage IOP.

SUMMARY

The present disclosure advantageously describes a chronotherapeutic system designed to administer therapies based on patient-specific physiological cues. A chronotherapeutic approach, that is, an approach synchronized with circadian rhythms, to pharmacotherapeutic management of glaucoma may be a beneficial part of a comprehensive POAG treatment paradigm. For example, an eye-mountable device (e.g., a contact lens) can be transformed into closed-loop, combination-therapy drug delivery systems that can optimize patient specific regimens through direct measurement of IOP and simultaneously address poor patient compliance and ultimately improve therapy results.

In some aspects, the present disclosure provides a smart contact lens featuring a chronotherapeutic delivery system for the treatment of primary open-angle glaucoma which enables therapeutic products to be delivered to the eye in a controlled manner only when desired. Embodiments of the present disclosure include one or more of the following features: integrated IOP monitoring, integrated pulsatile drug delivery, and a chronotherapeutic closed-loop operation based on patient specific physiological responses.

According to one embodiment, an eye-mountable device comprises a substrate having an eye-mounting surface configured to be positioned on an eye of a patient, a sensor coupled to the substrate and operable to obtain a plurality of measurements representative of a condition of the eye of the patient over a period of time, a therapeutic agent delivery assembly coupled to the substrate, and a processor for executing a temporal model of a therapeutic agent delivery in communication with the sensor and the therapeutic agent delivery assembly. The processor is operable to receive the plurality of measurements and to activate the therapeutic agent delivery assembly to administer a first amount of a drug to the eye of the patient based on the temporal model associated with the plurality of measurements.

In some embodiments, the substrate comprises a contact lens. The sensor comprises an inductor loop including a diameter. The diameter of the inductor loop is configured to increase or decrease based on an intraocular pressure of the eye of the patient, and the processor is configured to measure the intraocular pressure based on the diameter of the inductor loop. In some aspects, the sensor comprises a resonant impedance sensor controlled by the processor to take multiple measurements spaced in time. The therapeutic agent delivery assembly comprises one or more therapeutic agent reservoirs and a thin film coupled to each of the one or more therapeutic agent reservoirs. The thin film is controlled by the processor and operable to dissolve to release a therapeutic agent to the eye of the patient.

In some embodiments, the temporal model is based on a circadian rhythm of the patient. In some embodiments, the temporal model is based on physiological data corresponding to the patient. In some embodiments, the temporal model is generated and maintained by an adaptive neural network. In some aspects, the temporal model comprises a therapeutic agent delivery schedule. In another aspect, the sensor and the therapeutic agent delivery assembly are configured to operate in a closed loop.

According to another embodiment, a method for delivering a therapeutic agent to an eye of a patient includes obtaining, by an eye-mountable sensor, measurements of a condition of the eye of the patient over a period of time, providing, by a processor coupled to the eye-mountable sensor, a temporal model corresponding to a physiological cycle of the patient, the temporal model based on the obtained measurements of the condition of the eye, and delivering, by a therapeutic agent delivery assembly coupled to the eye-mountable sensor, an amount of a therapeutic agent to the eye of the patient based on the temporal model.

In some embodiments, obtaining the measurements of the condition of the eye of the patient comprises measuring a resonant impedance by the eye-mountable sensor. In some embodiments, the method further comprises modifying the temporal model based on the obtained measurements. In some embodiments, the temporal model is based on a circadian rhythm of the patient. In some embodiments, the temporal model is based on physiological data corresponding to the patient. In another embodiment, the temporal model is generated and maintained by an adaptive neural network. In some aspects, the temporal model comprises a therapeutic agent delivery schedule.

In some embodiments, delivering the therapeutic agent to the eye of the patient comprises applying a voltage to a thin film disposed on a therapeutic agent reservoir to dissolve the thin film. In another embodiment, the steps of obtaining and delivering are performed by the processor in a closed loop.

According to another embodiment, an eye-mountable device comprises an intraocular pressure (IOP) sensor coupled to a contact lens, the IOP sensor comprising an inductor loop having a diameter configured to change in response to a change in an IOP of the eye of the patient, a reservoir coupled to the contact lens and comprising a therapeutic agent and a film positioned over an opening in the reservoir to seal the therapeutic agent within the reservoir, and a processor coupled to the contact lens and in communication with the IOP sensor and the reservoir. The processor comprises a temporal model and is configured to receive IOP measurements from the IOP sensor, and activate the reservoir to release the therapeutic agent to the eye of the patient by applying a voltage to the film. The temporal model comprises time-dependent instructions for releasing the therapeutic agent to the eye of the patient, and the processor activates the reservoir according to the temporal model.

In some embodiments, the temporal model is based on a circadian rhythm of the patient. In some embodiments, the temporal model is based on physiological data corresponding to the patient. In another embodiment, the temporal model is generated and maintained by an adaptive neural network. In one aspect, the IOP sensor and the reservoir are configured to operate in a closed loop. In another aspect, the temporal model is updated based on the received IOP measurements.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which:

FIG. 6A is a cross-sectional view of an eye-mountable IOP therapy device, according to some aspects of the present disclosure.

DETAILED DESCRIPTION

Figure 1:
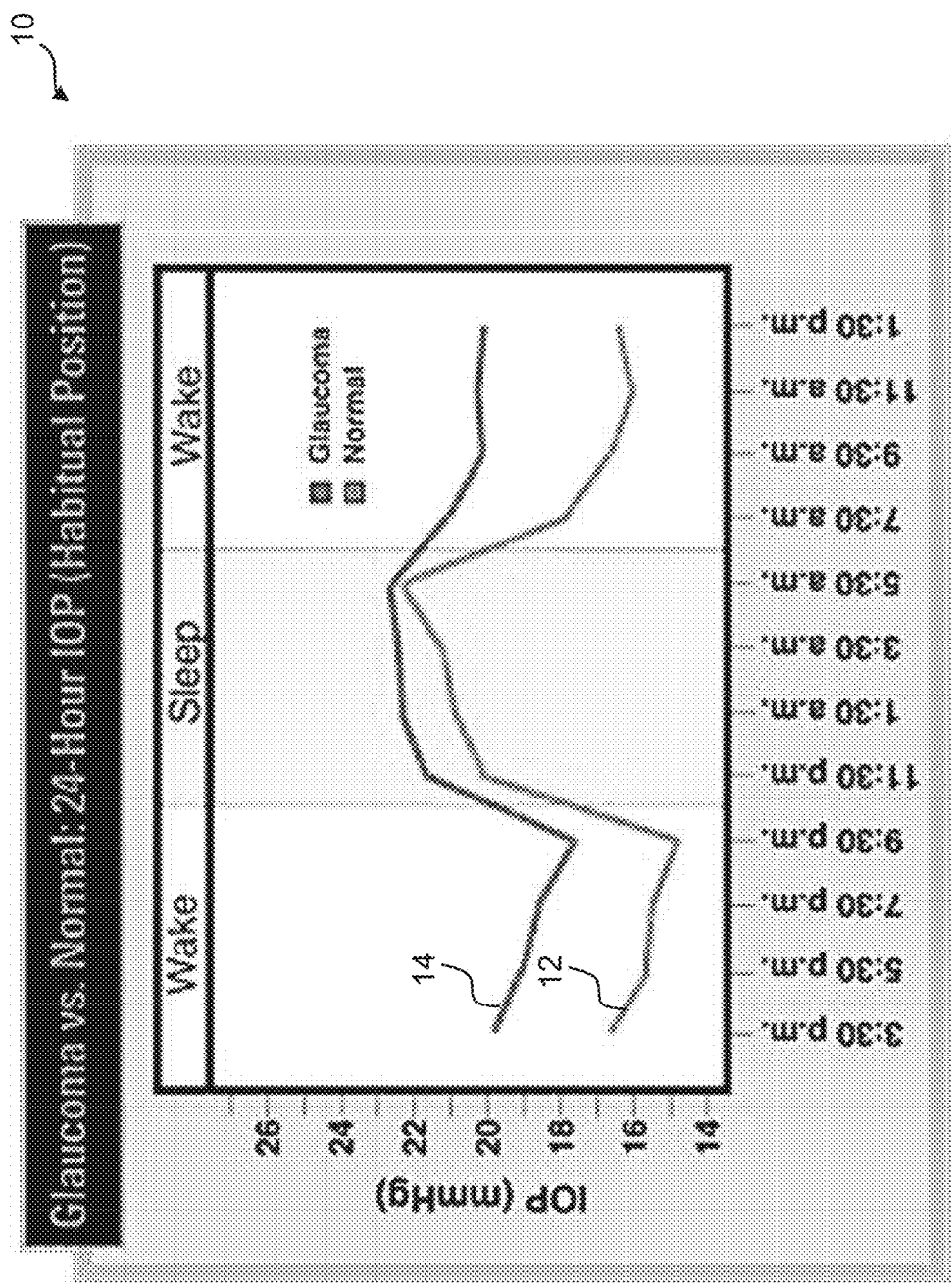
FIG. 1 is a graphical view of a plurality of intraocular pressure (IOP) measurements obtained from a healthy patient and a patient with glaucoma over a period of approximately 24 hours, according to some aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. For example, while the therapeutic devices are described in terms of eye-mountable devices configured to measure intraocular pressure, it is understood that it is not intended to be limited to this application. The devices and systems are equally well suited to any application requiring physiological measurements of an eye of a patient. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

The present disclosure provides chronotherapeutic devices, systems, and methods for treating conditions of a patient's eye. A chronotherapeutic approach can be implemented by a therapeutic product that contains a dynamic element such as a delivery system, such that the therapeutic agent is delivered at the time when it is needed. In chronopharmacotherapy, drug administration is synchronized with circadian rhythms. If the peak of symptoms occurs at daytime for example, a conventional dosage form can be administered just before the symptoms are worsening. If symptoms of the disease became worse during the night or in the early morning the timing of drug administration can coincide with onset or end of wear schedules.

In the context of glaucoma, this disclosure provides solutions to the challenges described above by enabling non-invasive closed-loop drug delivery to the eye from a smart contact lens based on integrated on-board IOP monitoring and programmable drug delivery. Patients can insert a smart contact lens into their eye and their specific personalized therapy is delivered seamlessly throughout the day synchronized to their IOP circadian rhythm without the need to carry multiple drops or keep track of schedules. More generally, the device 110 can enable customized combination-therapy delivery profiles which are currently impossible or impractical with topical administration. In cases where the therapeutic window changes or is cyclic (e.g., due to circadian rhythms such as in glaucoma), the device 110 is able to meet these changes in a customized manner appropriate for each patient.

Figure 2:
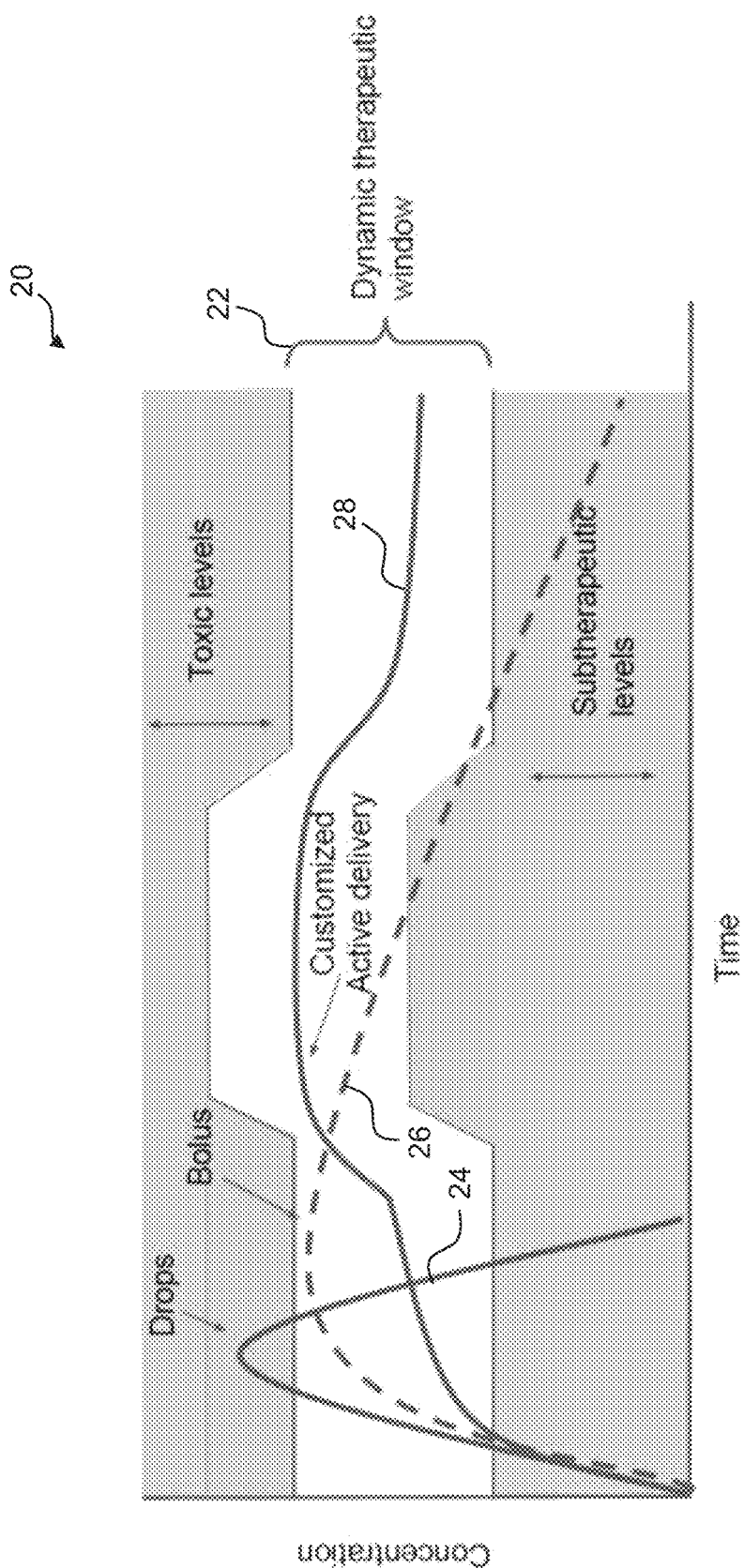
FIG. 2 is a graphical view of a time-dependent dynamic therapeutic window for a therapeutic agent applied to a patient's eye, according to some aspects of the present disclosure.

Applying a chronotherapeutic approach to therapy contemplates not only the time at which the therapeutic agent is administered, but also the amount of the agent administered at a given time. FIG. 2 is a graphical representation of a dynamic therapeutic window 22 for treating glaucoma with a chronotherapeutic agent. The y-axis represents a concentration of the agent, such as a drug, and the x-axis represents time over a period of a day. The dynamic therapeutic window 22 illustrates a time-dependent range of concentrations of the agent that are effective (i.e., not subtherapeutic), but not so high as to be toxic. The circadian rhythm of the patient can be observed in the dynamic therapeutic window 22. For example, the effective, non-toxic range of drug concentrations shifts to higher concentrations for a period of time each day (e.g., during the night).

FIG. 2 also shows concentration curves 24, 26, 28 for various drug-delivery mechanisms. For example, a first curve 24 shows a change in concentration of therapeutic eye drops over time. Eye drops may rapidly deliver a high concentration of the therapeutic agent, so much as to exceed toxicity limits. However, the concentration of the therapeutic agent quickly declines to subtherapeutic levels after only a short period of time. In other words, therapeutic eye drops may have a short residence time, which can lead to suboptimal therapeutic results. A second curve 26 shows a change in concentration of a bolus of a therapeutic agent administered into the eye. The Bolus may not exhibit the same sharp increase in concentration as the drop, illustrated by the first curve. Furthermore, the Bolus may offer increased residence time, shown as a relatively gradual decline compared to the first curve. However, the concentration of the Bolus may fall to subtherapeutic levels after a period of time, and may not be responsive to the time-dependent dynamic therapeutic window effected by the circadian rhythm of the patient.

A third curve 28 illustrates the concentration of a therapeutic agent administered according to a dynamic, customized, active delivery system. In one embodiment, the active delivery model is adapted to the specific physiological cycles of the patient, and maintain a concentration of a therapeutic agent within the dynamic therapeutic window 22 of the patient. For example, as the time-varying physiology of the patient changes and calls for an increased amount of the therapeutic agent, the active delivery model can respond to and/or predict such changes to continuously maintain an appropriate concentration of the therapeutic agent delivered to the eye.

Figure 3:
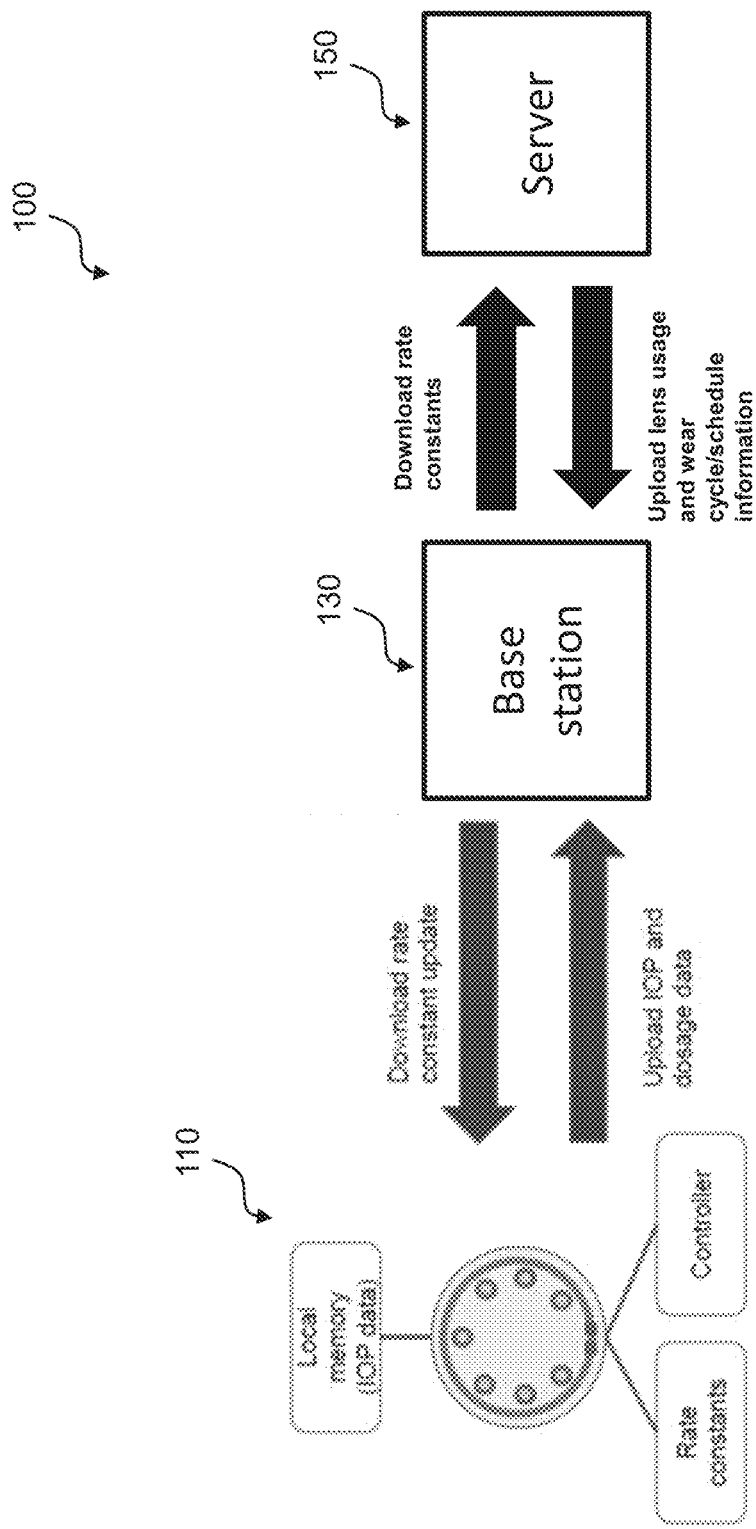
FIG. 3 is a diagrammatic view of a closed-loop IOP therapy system, according to some aspects of the present disclosure.

FIG. 3 depicts a system 100 for closed-loop intraocular therapy, according to aspects of the present disclosure. The system 100 includes an eye-mountable therapy device 110, a base station 130, and a server 150. The eye-mountable therapy device 110 can be periodically in communication with the base station 130 to exchange data and/or recharge power storage in the device 110. For example, in some embodiments, the eye-mountable therapy device 110 comprises a contact lens, and the base station 130 comprises a storage container for safeguarding the device 110, lubricating and cleaning the device 110, recharge an onboard battery of the device 110, and/or exchange data with the device 110. In one embodiment or mode of operation, a patient places the device 110 in a fluid reservoir of the base station 130 overnight, the fluid reservoir containing, e.g., saline solution, cleaning solutions, lubricating solution, and/or sanitizing solutions. The patient then returns the device 110 to the patient's eye when the patient wakes up. In one embodiment, the base station 130 comprises a fluid reservoir, and a plurality of electronic components, such as an inductive charger, a wireless communication device (e.g., Bluetooth®, near-field communication (NFC), radio-frequency (RF), medical implant communication service (MICS), infrared) a microcontroller, and a memory device.

Data exchanged between the device 110 and the base station 130 takes the form of any suitable technique, such as Bluetooth®, MICS, RF data, infrared, near field communication (NFC), etc., and includes patient-specific information relating to a temporal model of a therapeutic agent delivery system, such as rate constants, updated temporal models, therapeutic agent delivery schedules, IOP values measured by the device 110, dosages administered by the device 110, compliance confirmation, and any other useful information for operating a closed-loop therapy system. The base station 130 is in communication with the server 150, which can comprise a cloud-based database in some embodiments. The server 150 stores information and/or provides processing resources for data provided from the device 110 and/or the base station 130. In some embodiments, the server 150 stores an IOP performance history and current health status of the patient, including blood pressure, sleep schedules, medication refill history and schedules, current medications, known health conditions, diseases, activity, age, etc.

In some embodiments, the base station 130 also includes a communication interface, such as a graphical display configured to indicate refill schedules, compliance metrics, IOP history, disease management metrics, reminders, and connectivity with social and support networks to a user. In some embodiments, the server 150 stores and provides predictive models including pharmacokinetic/pharmacodynamic (PK/PD) for drug combinations that utilize the patient's IOP data to optimize rate constants associated with the temporal model of the therapeutic agent delivery assembly of the device 110. In some embodiments, the temporal model includes factors such as pharmaceutical half-life of an administered therapeutic agent, bioactive species clearance constants, patient-specific aqueous humor production/efflux rates, and/or any other relevant concomitant health factors. In alternative embodiments, the base station 130 is not in communication with the server 150 and performs the functions described above with respect to the server 150, such as storing and providing predictive models, provide processing of the patient's physiological data relevant to the temporal model and therapeutic agent delivery schedules, storing IOP performance history and current health status of the patient, and any other relevant function useful in facilitating the closed-loop function of the device 110.

Therapeutic agents delivered by the device 110 include one or more substances, such as pharmaceutical agents, drugs, chemicals, solutions, compounds, or any other suitable therapeutic agent. For example, in some embodiments, the device 110 is configured to administer one or more of a prostaglandin, a beta blocker, an alpha-adrenergic agonist, a carbonic anhydrase inhibitor, or any pharmaceutical agent configured to be delivered to the eye of the patient. In some embodiments, the device 110 delivers more than one of the foregoing either in combination simultaneously or staged such that the initial release of a first agent is spaced in time form the release of a second agent.

Figure 4:
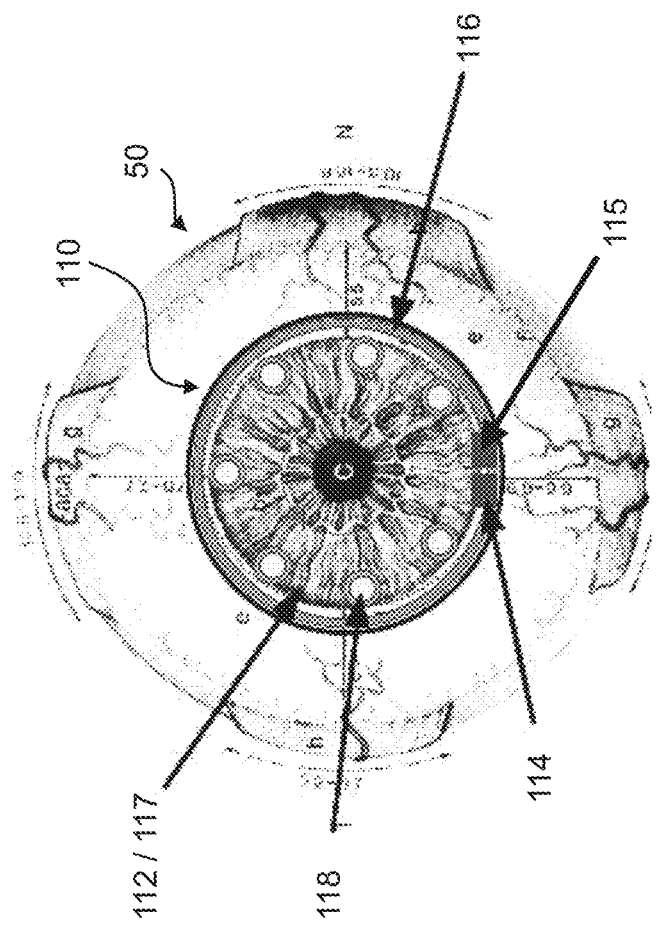
FIG. 4 is a perspective view of an eye-mountable IOP therapy device positioned on a patient's eye, according to some aspects of the present disclosure.

FIG. 4 depicts a perspective view of the therapeutic device 110 of FIG. 3 positioned on an eye 50 of a patient. The device 110 includes a flexible substrate 112, and a plurality of electronic components mounted to the substrate 112. The electronic components mounted to the substrate 112 include a processor or controller 114, a power supply 115, an intraocular pressure sensor 116, and a therapeutic agent delivery assembly 118. The substrate 112 and electronic components are surrounded by a flexible coating 117 biologically compatible with the patient's eye 50. For example, the flexible coating 117 includes a silicone hydrogel, in some embodiments. In the embodiment of FIG. 4, the substrate 112 comprises a contact lens. The contact lens 112 is configured to provide vision correction, in some embodiments. In other embodiments, the contact lens does not correct vision.

The processor 114 comprises one or more electronic devices in communication with the IOP sensor 116 and the therapeutic agent delivery assembly 118. For example, in some embodiments, the processor 114 comprises one or more of an application-specific integrated circuit (ASIC), a field-programmable gate array (FPGA), microprocessor, passive electronic devices (e.g., resistors, capacitors, inductors), memory devices, data storage devices, power storage devices (e.g., batteries), or any other suitable electronic device. In the embodiment shown in FIG. 4, the processor 114 is coupled to the power supply 115. The power supply 115 includes power storage means, such as batteries and/or capacitors along with inductive coils to receive power and power management control circuitry. In some embodiments, the processor 114 comprises fewer or more electronic devices, such as one, three, four, five, six, or any other suitable number of electronic devices.

The processor 114 is in communication with the IOP sensor 116 and configured to receive a plurality of measurements representative of the IOP. As explained further below, the sensor 116 shown in FIG. 4 comprises a resonant impedance sensor including an inductor loop with a diameter configured to change as the IOP of the eye changes the geometry of the eye 50. The processor 114 is also in communication with and configured to control the therapeutic agent delivery assembly 118. As will be explained further below, the therapeutic agent delivery assembly 118, or drug delivery assembly 118, comprises one or more reservoirs containing a therapeutic agent, such as a drug, and a thin film seal disposed over the reservoir, such that the thin film seal can be opened (i.e., dissolved or thermally actuated) or actuated on command by the processor 114 to release the therapeutic agent to the eye 50 through the cornea.

The device 110 also comprises an antenna coupled to the processor 114 for communication, programming, and/or power transfer purposes, in some embodiments. The electronics are disposed on a polymer substrate 112, which includes at least one of PMMA, Parylene, PET, polyurethane, polyimide, rigid gas permeable fluorosilicone acrylate, liquid crystal polymer, silicon-based polymers, silicone acrylate and the like. The device 110 is further encapsulated and formed in a soft flexible biocompatible material 117 suitable for ocular wear, such as polymeric material like polymethylmethacrylate ("PMMA"), polyhydroxyethylmethacrylate ("polyHEMA"), silicone hydrogel, silicon based polymers (e.g., flouro-silicon acrylate), silicone elastomer or combinations thereof.

Figure 5:
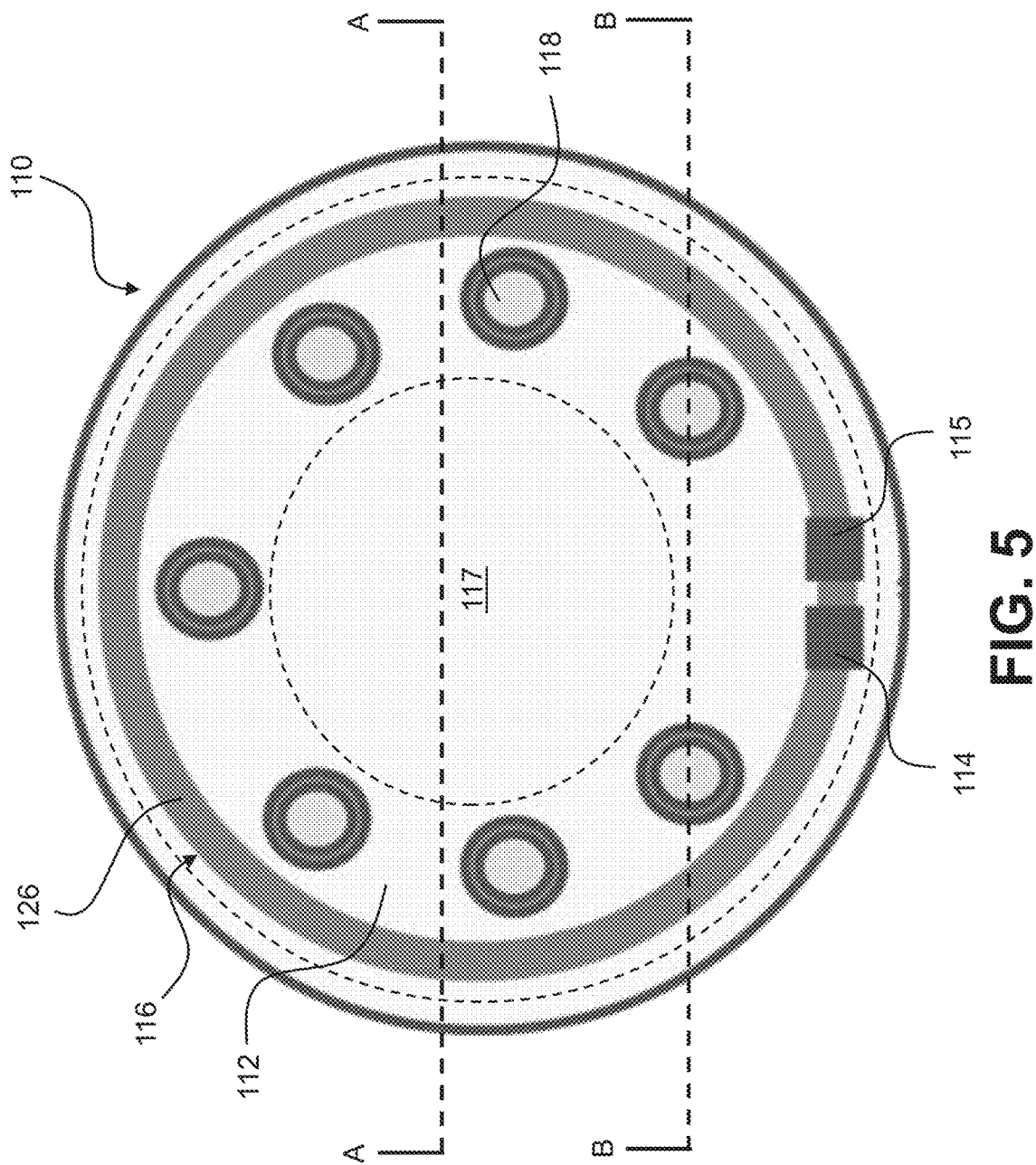
FIG. 5 is a front view of an eye-mountable IOP therapy device, according to some aspects of the present disclosure.

FIG. 5 is a front view of the eye-mountable therapy device 110 of FIG. 4. The device 110 comprises a plurality of electronic components, including a processor 114 in communication with an IOP sensor 116 and a therapeutic agent delivery assembly 118, and a power storage device 115. The therapeutic agent delivery assembly 118 comprises a plurality of therapeutic agent-containing reservoirs. The processor 114, IOP sensor 116, therapeutic agent delivery assembly 118, and power storage device 115 are mounted to a substrate 112. The IOP sensor 116 is formed along the circumference of the device 110 and is in communication with the processor 114. The IOP sensor 116 comprises an inductor loop 126 communicatively coupled to a capacitor, which forms a resonant circuit in communication with the processor 114. The inductor loop 126 is formed along a circumference of the substrate 112 and comprises a diameter configured to change according to a change in IOP of the patient's eye. The processor 114 can measure or detect changes in the resonance of the IOP sensor 116 formed by the inductor loop 126 and the matching capacitor.

The substrate 112 is encapsulated by, or embedded in, a flexible coating 117, as described above. The flexible coating 117 comprises a material similar or identical to those used in contact lenses, such as a silicone hydrogel. In some embodiments, the flexible coating 117 is shaped around the substrate 112 and electronics such that the device 110 is sized and shaped to function as a contact lens. In some embodiments, the coating 117 is shaped to provide vision correction according to a prescription.

FIG. 6A depicts a cross-sectional view of the device 110 along the line A-A. The cross-sectional view shows the device 110 at two distinct diametric positions 111, 113, each of which is associated with a distinct IOP of the patient's eye. The diameter can be defined as the diameter of an inner edge of the inductor loop 126. As the IOP of the patient's eye changes, the geometry of the eye (e.g., shape, corneal diameter, size, etc.) also changes. Consequently, the diameter, and therefore the inductance, of the inductor loop 126 of the IOP sensor 116 also changes, which results in a change in the resonance of the circuit of the IOP sensor 116 that can be measured by the IOP sensor 116. In that regard, a first diametric position 111, associated with a first IOP, can be described as having a diameter d, and a second diametric position 113, associated with a second IOP, can be described as having a diameter d+Δd. Although shown in terms of diameter in FIG. 5, the relationship between IOP and the geometry of the IOP sensor 116 can also be described in terms of radius, such as a corneal radius, or a radius of the inductor loop 126.

The relationship between the change in corneal radius and change in IOP is linearly related for small pressure changes and thin membranes such as the cornea. For example, an IOP change of 1 mmHg may generate a ~3 um change in corneal radius (for an eye with corneal radius of curvature of 7.8 mm) The relationship may be expressed as:

$$\Delta IOP = \Delta r/c$$

where $\Delta r$ is the change of the radius of curvature and c is dependent on the biomechanical properties of the eye. Thus, for an IOP range spanning ~10-30 mmHg a maximum change of 120 μm in corneal diameter can be expected. As explained above, the change in corneal diameter results in a change in the diameter or radius of the inductor loop 126. For changes in radius much smaller than the designed radius $r_0$ of the inductor loop 126 (e.g., $\Delta r \ll r0$), the inductor loop inductance L is approximately linearly related to the change in IOP, that is $\Delta L = \alpha \Delta IOP$ where $\alpha$ is a constant determined primarily by the inductor loop 126 design and biomechanical properties of the eye.

A matching capacitor for the IOP sensor 116 is integrated within the processor 114 in such a manner as to create a resonant circuit with the inductive loop. The resonance of this circuit is measured by the processor 114 with respect to changes in IOP. In some embodiments, the circuit is operated in a low-power configuration such that only start-up characteristics including start-up time or start-up current can be employed as means to detect IOP induced changes in the resonant circuit response. IOP may be a slowly varying signal that produces incremental changes over the course of hours. It is therefore expected that this sensor approach may only involve intermittent activation for example every 15-30 minutes with a small time-averaged measurement (e.g., 10 seconds). A plurality of such intermittent measurements serve to keep data storage use as low as possible. In some embodiments, the system algorithmically removes extraneous noise elements such as blinks, or operates at a low enough sampling frequency (<3 hz) such that these elements may be averaged or excluded from the plurality of measurements. The IOP sensor 116 may be factory calibrated but may also make use of patient-specific calibrations performed with standard ocular tonometry equipment in a clinician's office or through at-home systems.

While the embodiment of FIG. 5 includes a resonant impedance sensor 116, the present disclosure contemplates that the change in corneal diameter is measured in a contact lens through a variety of mechanisms which includes piezoresistive, electrochemical impedance, or capacitive means. For example, in some embodiments the sensor 116 measures geometry-dependent electrochemical signals such as solution impedance. For example, electrochemical impedance spectroscopy (EIS) may be implemented to detect changes in corneal radius. This measure occurs between at least two electrodes that may be placed near the periphery of the lens. Although the matching capacitor is incorporated into the processor 114 in the embodiment of FIG. 5, in alternative embodiments, the matching capacitor is a discrete component electrically connected to the inductor loop 126.

Figure 6B:
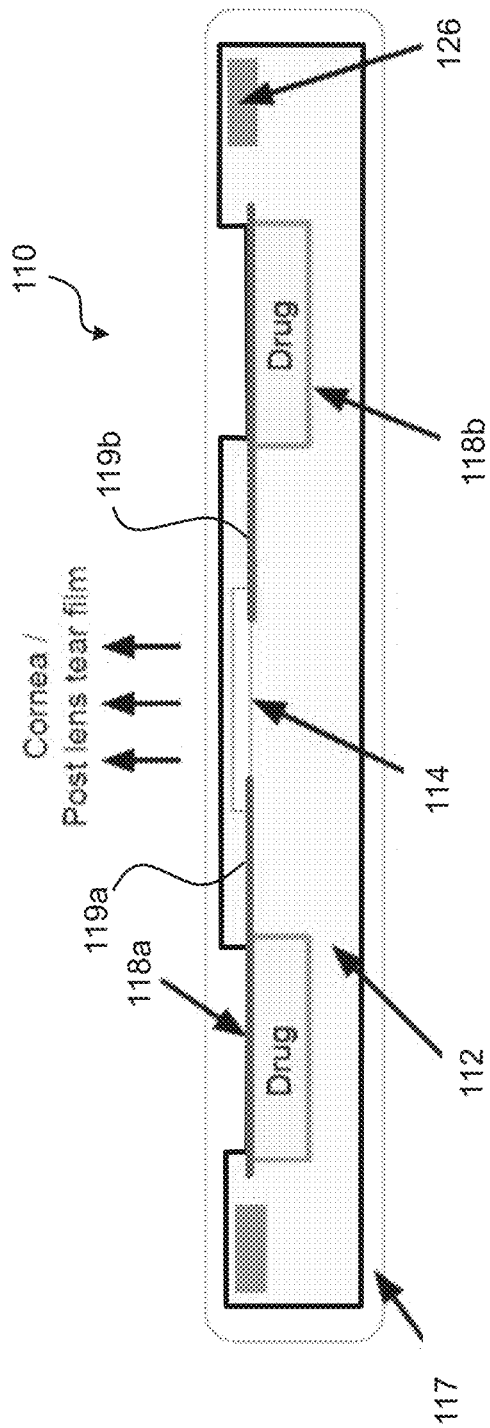
FIG. 6B is a cross-sectional view of an eye-mountable IOP therapy device, according to some aspects of the present disclosure.

FIG. 6B is a cross-sectional view of the device along the line B-B, and illustrates the therapeutic agent delivery assembly 118 of the device 110. The device 110 comprises standard contact lens materials such as silicone, silicone hydrogels, rigid gas permeable polymers, PMMA, polyurethane, Parylene, PET, polyimide or combinations thereof. The therapeutic agent delivery assembly 118 may also be referred to as a drug delivery assembly, in some instances. The therapeutic agent delivery assembly 118 includes a plurality of therapeutic agent reservoirs 118a, 118b, and a plurality of controllable thin film seals 119a, 119b positioned over the reservoirs 118a, 118b on a corneal side of the device 110. The reservoirs 118a, 118b are integrated into the substrate 112 within the device 110 and store a known quantity of drug. The reservoirs 118a, 118b can be compatible with various physical forms of drug including aqueous solutions, gel, suspensions, microemulsions, nanoparticles, liposomes, dry (powder) or combinations thereof. In one embodiment, the reservoir(s) 118a, 118b range in volume from 1 pL-100 nL and are lined with a passive, inert coating such as $SiO_2$, $Al_2O_3$, cyclic olefin polymers (COP), polyethylene, polypropylene, PET or other substantially inert drug-contacting material. The reservoir(s) 118a, 118b provide a means for sterile storage of a drug to allow for on-demand release and delivery at a programmed time thereby providing a therapeutic effect on the eye via targeted transcorneal absorption.

The thin film seals 119a, 119b, are in communication with and controlled by the processor 114. In that regard, the processor 114 is configured to cause each of the seals 119a, 119b to undergo electrodissolution by applying a voltage to the thin film seals 119a, 119b. Each of the seals 119a, 119b is single-use and opened on-demand electronically to allow the therapeutic agent within the reservoirs 118a, 118b to diffuse out towards a corneal surface of the eye. The seal opening action initiates drug release into the thin post-lens tear film located between the device and the cornea. The combination of a very thin post-lens tear film (1-3 um) and directed drug release to the corneal surface provides a quasi-static environment that promotes an increased drug residence time (>30 minutes vs. ~30 seconds for topical administration) resulting in greater bioavailability of drug at the corneal surface thus maximizing transcorneal absorption and anterior segment bioavailability.

In some embodiments, drug release is activated electronically through application of a low-level voltage stimulus to the thin film comprising the seal. This thin film forms a physical seal on a side of the reservoir which is ideally positioned against the cornea. The metallic film undergoes electrodissolution when a potential is applied in presence of chloride-containing solutions (e.g., tear film). The mechanism is described through the following equilibrium equations with the rate limiting step being the activated desorption of the gold complex from the surface.

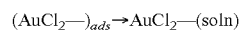

In some embodiments, Gold is chosen as a membrane material because it is easily deposited and patterned, has a low reactivity with other substances and resists spontaneous corrosion in many solutions over the entire pH range. Gold is also a biocompatible material. However, the presence of a small amount of chloride ion, as is naturally found in tear fluid, creates an electric potential region which favors the formation of soluble gold chloride complexes. Holding the anode potential in this corrosion region (~1V) enables reproducible gold dissolution of films approximately 50-500 nm thick. Potentials below this region are too low to cause appreciable corrosion, whereas potentials above this region result in gas evolution and formation of a passivating gold oxide layer that causes corrosion to slow or stop. Other metals such as copper or titanium tend to dissolve spontaneously under these conditions or do not form soluble materials on application of an electric potential. Although gold is used as a model compound in this description, other inert materials may be used to achieve similar electrodissolution-mediated drug release (e.g., Ti, Pd, Pt, Ir, Ir—Pt alloys).

Figure 7:
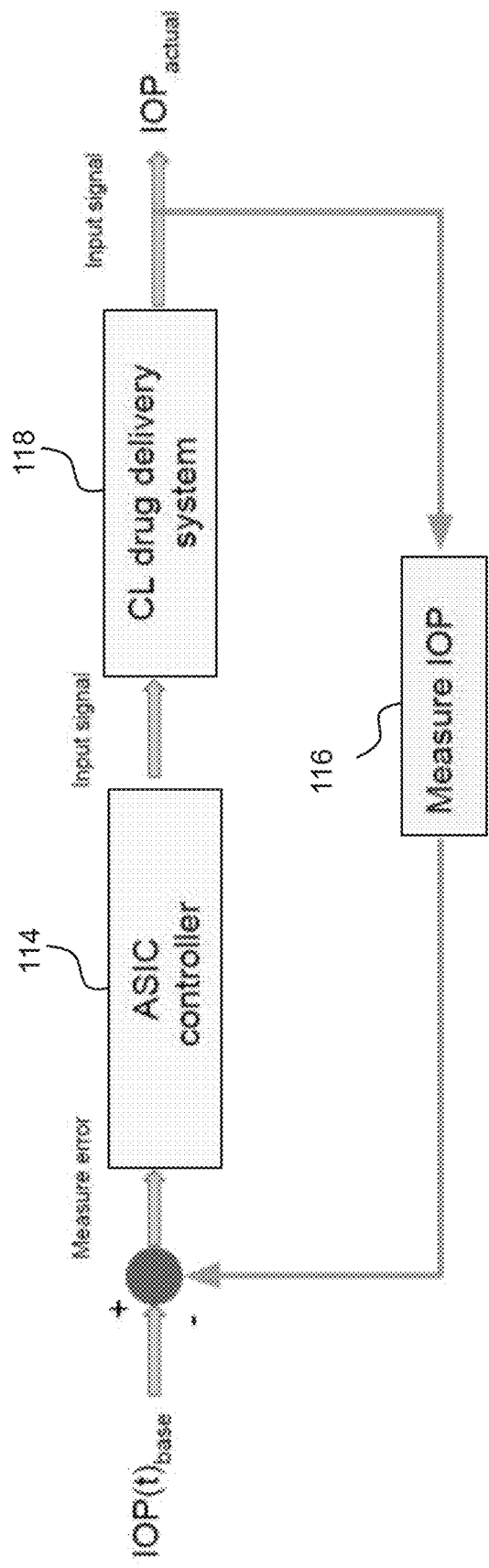
FIG. 7 is a diagrammatic view of a closed-loop operation of an eye-mountable IOP therapy device, according to some aspects of the present disclosure.

FIG. 7 is a diagram illustrating a closed loop IOP control system. As mentioned above, in some embodiments, the device 110 is configured to operate in a closed-loop fashion for a period of time (e.g., daily), such that the IOP measurement and the chronotherapeutic administration of therapeutic agents are performed by the device 110 without the need for intervention by physicians or the patient. The closed loop operation of the device 110 is shown in FIG. 7 as the loop performed among the processor (or ASIC controller) 114, the drug delivery assembly 118, and the IOP sensor 116. The processor 114 operates according to a temporal model, which can include a therapeutic agent delivery schedule, diffusion rate constants, drug permeation constants, drug residency time values, drug half-life values, target and measured IOP values for the patient, wear time duration (e.g., number of hours), days of device usage (e.g., day 1 vs. day 10) and other relevant information. The temporal model utilizes proportional, integral, and derivative (PID) control terms, individually or in combination, to achieve closed loop control.

Referring to FIG. 7, $IOP(t)_{base}$ is the patient specific healthy target circadian IOP baseline. $IOP_{actual}$ is IOP the real-time IOP as measured by the on-board IOP sensor. In this embodiment, a the processor 114 first detects $IOP_{actual}$ and adjusts the amount of the therapeutic agent delivered based on a PID transfer function of deviation error from $IOP(t)_{base}$. In some embodiments, the processor 114 compares against historical patient-specific IOP data recorded during the last 24 hours, for example. In one embodiment or mode of operation, the adjustment to the processor's delivery of the therapeutic agent is made during a single 24 hour time period. In another embodiment or mode of operation, the adjustment is implemented across one or more 24 hour periods.

Additionally, during standard overnight lens disinfection times the processor uploads and updates the patient's IOP performance data, which may span hours, days, or weeks, to a server, such as a cloud-based database. Updated rate constants and transfer function coefficients are then downloaded to optimize controller performance. In some embodiments, the processor 114 further implements predictive pharmacokinetic/dynamic (PK/PD) models to refine control over the course of hours to days. The models include factors such as pharmaceutical half-life, bioactive species clearance constants and patient specific aqueous humor production/efflux rates. For example, the estimated half-life of the active ingredient of latanoprost, latanoprost acid, is ~2.8 hours in aqueous humor. Other formulations such as beta-blockers (e.g., betaxolol and timolol maleate) are formulated as salts with onset of action generally noted within about 30 minutes and the maximum effect can usually be detected about 2 hours after topical administration. Thus, on board PK/PD prediction allows for optimized patient regimens based on their specific physiological rate constants (e.g., aqueous humour production and efflux rates, corneal penetration rate, etc.) in conjunction with known PK/PD models for various drugs involved in their specific IOP management paradigm. This may be particularly useful in cases where monotherapy is insufficient and multiple drugs are prescribed increasing the complexity of care. In particular when the patient is not wearing the lens (e.g., overnight) the controller can reinitiate control based on overnight PK/PD prediction. In some embodiments, the device 110 is configured to be worn for extended periods of time, for example, overnight. In that regard, the device 110 can include a sufficient amount of therapeutic agent and battery capacity to perform a closed-loop chronotherapeutic model for a period of 24 hours or more, such as several days, or weeks.

In some embodiments, updating the temporal model of the device 110 includes sending, by the server, a notification to a physician of the patient. In some embodiments, the notification includes a request for authorization to change a dosage and/or dosing schedule of a therapeutic agent. In other embodiments, the notification includes a prompt for the physician to discretionarily adjust the dosage and/or dosing schedule based on recent IOP measurements obtained by the device 110. In still other embodiments, the server sends a notification to a health care provider relating to temporal model modifications that may be relevant for billing or other business purposes.

Figure 8:
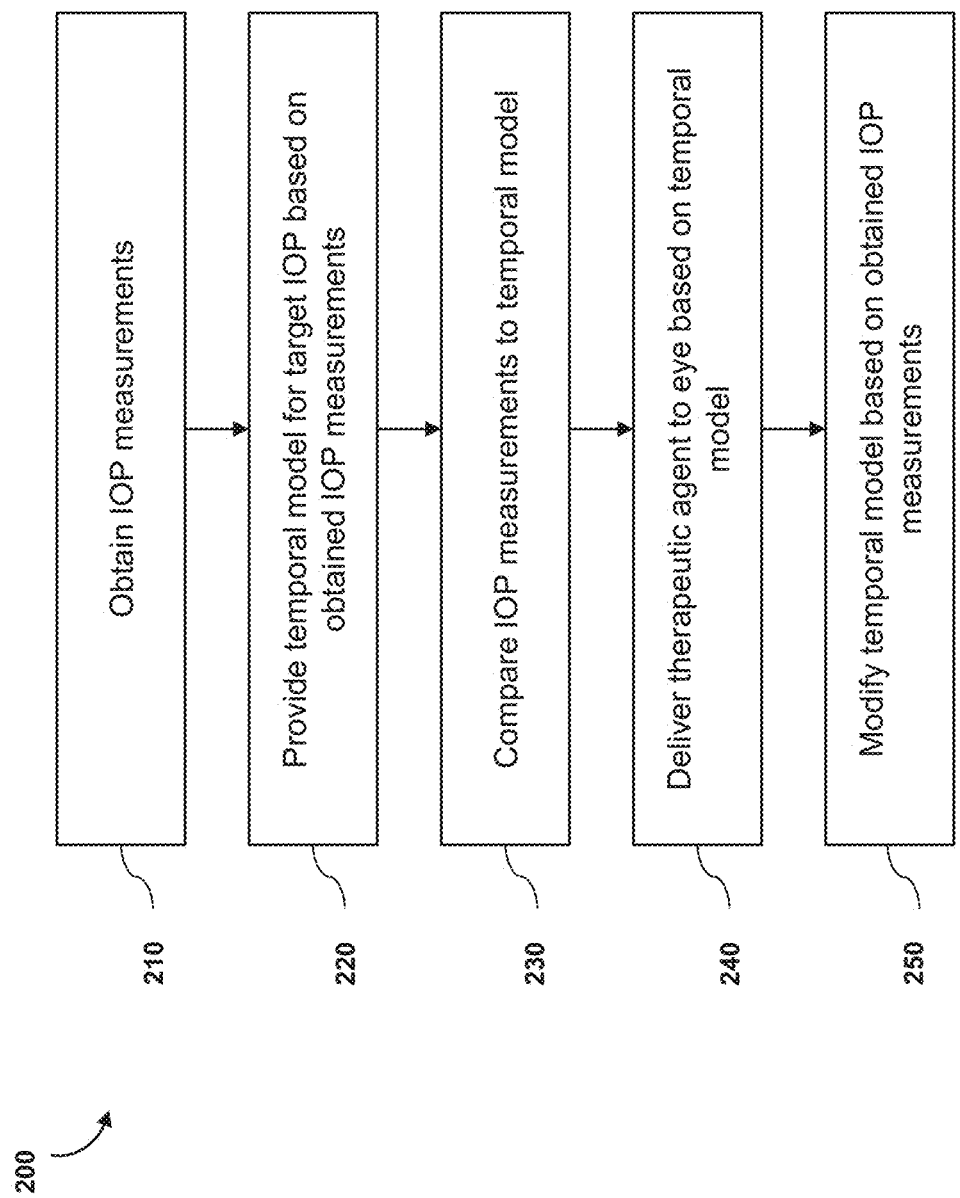
FIG. 8 is a flow diagram illustrating a method for closed-loop operation of an eye-mountable IOP therapy device, according to some aspects of the present disclosure.

FIG. 8 is a flow diagram illustrating a method for closed-loop therapy, according to some embodiments of the present disclosure. In step 210, a plurality of IOP measurements of a patient's eye are obtained by a wearable IOP sensor, such as the IOP resonant impedance sensor 116 of the eye-mountable device 110 shown in FIG. 5. In some embodiments, the IOP measurements are performed at predetermined time intervals. In some embodiments, the device 110 is configured to measure continuously for a period of time (e.g., throughout the day). As described above, the sensor is configured to operate in a low power consumption mode, in some embodiments, in order to prolong a battery life of the device, for example. In step 220, a temporal model is provided in the processor for achieving a target IOP based on obtained IOP measurements. In some embodiments, the temporal model is based on IOP measurements and/or other physiological data of the patient over a period of time, for example, several hours, days, weeks, months, or years. The temporal model includes instructions stored in a memory device of the processor for activating a therapeutic delivery assembly of an eye-mountable therapy device based on obtained IOP measurements. In some embodiments, the temporal model may comprise a drug delivery schedule customized for the patient's physiological rhythms.

In step 230, IOP measurements (e.g., $IOP_{actual}$, FIG. 7) are compared to the temporal model, which includes a target IOP (e.g., $IOP(t)_{base}$, FIG. 7). The target IOP includes one or more time-dependent thresholds that indicate when to deliver an amount of a pharmaceutical agent to the patient's eye. In some embodiments, the processor compares and/or applies IOP measurements obtained over a period of time to the temporal model to determine whether to administer a therapeutic agent, and what amount of the therapeutic agent is to be administered. In step 240, the processor activates the drug delivery assembly to release a therapeutic agent to the eye of the patient. Activating the drug delivery assembly comprises applying a voltage to one or more thin film seals positioned over one or more reservoirs containing a therapeutic agent. Applying the voltage to the thin film seals causes the thin film seals to undergo electrodissolution.

In step 250, the temporal model is updated based on IOP measurements obtained by the eye-mountable pressure sensor. For example, in some embodiments, the IOP measurements obtained by the pressure sensor over a period of time (e.g., day(s), week(s), month(s)) are uploaded to a server via a base station. When the patient places the eye-mountable device in the base station for overnight storage, the IOP measurements obtained throughout the day are automatically uploaded to the server through the base station, which is in communication with the server. The server analyzes and compares recently obtained IOP measurements with historic IOP measurements in order to determine whether and how the temporal model is to be modified or updated. In some embodiments, temporally-corresponding IOP measurements obtained over a period of several days, weeks, or months, are summed and averaged to generate a plot of average diurnal IOP measurements, which may be similar to the plots 12, 14 shown in FIG. 1.

The present disclosure contemplates various modifications to the method 200 described above. For example, in some embodiments, the temporal model is based on additional parameters, such as a pharmaceutical half-life of an administered therapeutic agent, bioactive species clearance constants, patient-specific aqueous humor production/efflux rates, and/or any other relevant concomitant health factors. In some embodiments, the temporal model is initially generated based on physiological data of a plurality of patients, or a patient non-specific temporal model. In some embodiments, the temporal model comprises a therapeutic agent delivery schedule, which includes instructions such as a time of day to administer the therapeutic agent, and what amount of the therapeutic agent should be administered. In that regard, in some embodiments, the temporal model comprises time-dependent instructions to administer a therapeutic agent that are independent of contemporaneous IOP measurements obtained by the device. For example, a drug delivery schedule of the temporal model may be created and/or updated according to IOP measurements obtained over a period of time, such as a day, several days, weeks, or months. In another embodiment, the temporal model is updated and refined through an adaptive neural network that resides in cloud-based server 150.

In some embodiments, a rate of release of the therapeutic agent can be controlled by, for example, controlling the geometry of the thin film seals that are dissolved. Although the present disclosure describes the drug delivery assembly as comprising therapeutic agent reservoirs that can be selectively opened by applying a voltage to a thin film seal, it will be understood that the present application contemplates other embodiments, assemblies, and mechanisms for delivering a therapeutic agent to the eye of the patient, such as electrothermic valves, pressure-driven (e.g., electrolytically generated pressure), electroosmotic flow, iontophoretic delivery, electrowetting, and other microfluidic-based approaches.

Figure 9:
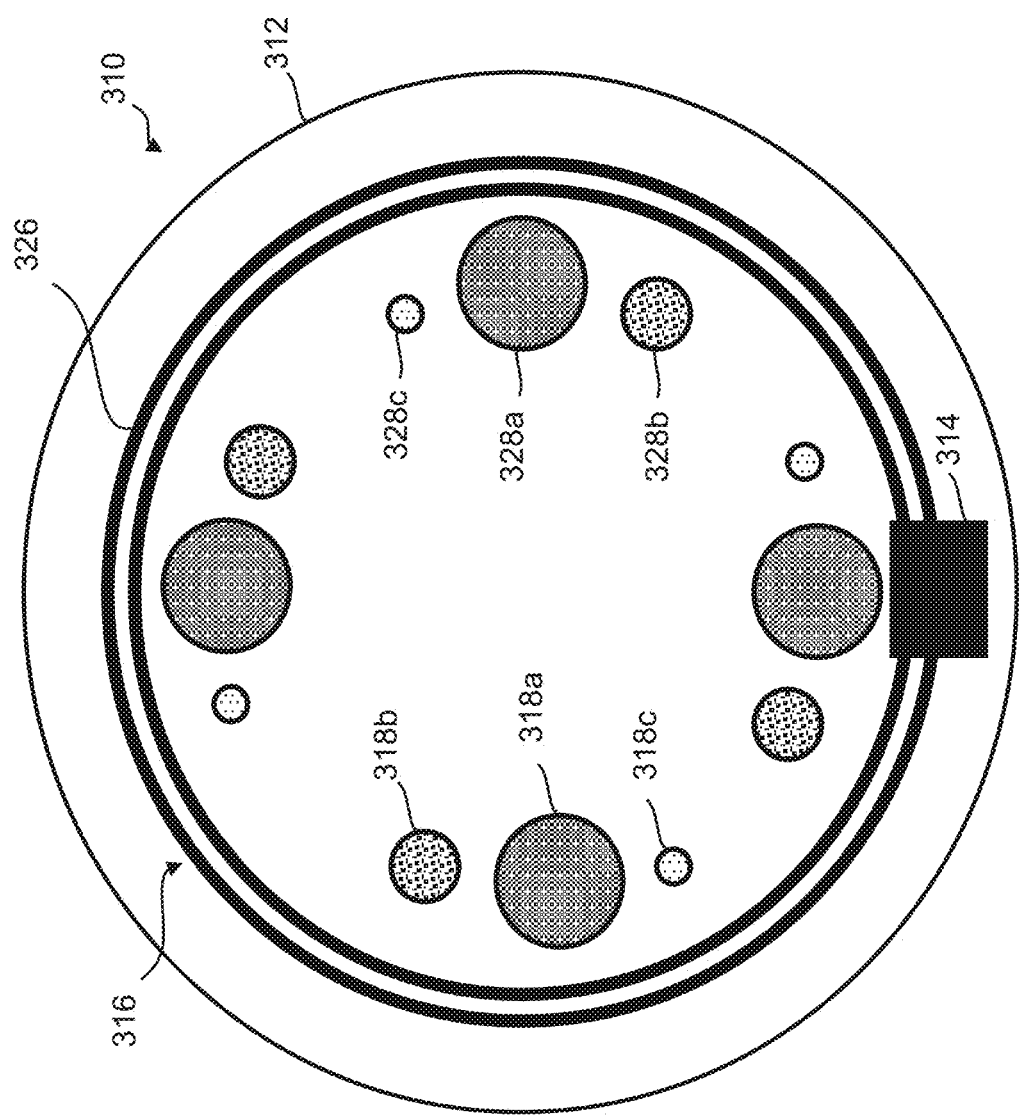
FIG. 9 is a plan view of an eye-mountable IOP therapy device, according to aspects of the present disclosure.

FIG. 9 depicts an eye-mountable therapy device 310 comprising a plurality of therapeutic agent reservoirs of different sizes, according to some embodiments of the present disclosure. The device comprises a plurality of reservoirs (e.g., 318a, 318b, 328a, 328b), each of which is contained and/or sealed by a thin film seal, such as the seals 119a, 119b, shown in FIG. 6. In the embodiment of FIG. 9, the therapeutic agent delivery assembly comprises reservoirs of different sizes. For example, a first large reservoir 318a comprises a first amount of a therapeutic agent, a first medium reservoir 318b may comprise a second amount of a therapeutic agent that is less than the first amount, and a first small reservoir 318c may comprise a third amount of a therapeutic agent less than the first and second amounts. Furthermore, in some embodiments, each of the reservoirs 318a, 318b, 318c comprise different therapeutic agents such that the processor 314 administers the therapeutic agents at different times or rates depending on the temporal model. In other embodiments, each of the reservoirs 318a, 318b, 318c comprise the same therapeutic agent such that the processor 314 administers a tailored amount of the agent by selectively opening the reservoirs to achieve the desired dosage based on the temporal model. In some embodiments, the first plurality of reservoirs 318a, 318b, 318c comprise a first type of therapeutic agent, and a second plurality of reservoirs 328a, 328b, 328c, comprise a second type of therapeutic agent. In other embodiments, one or more of the reservoirs comprises a combination of therapeutic agents. Similar to the device 110 shown in FIGS. 3-6, the device 310 shown in FIG. 9 comprises a substrate 312, and a processor 314 in communication with each of the reservoirs of the therapeutic agent delivery assembly and a physiological sensor 316, which comprises an inductor loop 326.

Although described in the context of glaucoma, IOP, and contact lenses, it will be understood that the present disclosure contemplates other variations of the devices, systems, and methods, for obtaining measurements representative of a condition of the eye, and treating the condition with a wearable therapy device. For example, in some embodiments, other types of an eye-mountable chronotherapy device can be used to treat dry eyes. In that regard, in alternative embodiments, an eye-mountable therapy device is configured to deliver a therapeutic agent to the eye to treat one or more symptoms of dry eyes, such as lubricants, pharmaceutical agents, anti-inflammatory drugs, etc., based on a temporal model. In an alternative embodiment, and eye-mountable therapy device is configured to deliver a therapeutic agent to the eye to treat one or more symptoms of ocular inflammation or infection, for example following surgery. In this embodiment, a pH sensor monitors the level of inflammation and provides closed-loop delivery control of anti-inflammatory drugs, steroids, or antibiotics based on a temporal model.

Generally, any creation, storage, processing, and/or exchange of user data associated the method, apparatus, and/or system disclosed herein is configured to comply with a variety of privacy settings and security protocols and prevailing data regulations, consistent with treating confidentiality and integrity of user data as an important matter. For example, the apparatus and/or the system may include a module that implements information security controls to comply with a number of standards and/or other agreements. In some embodiments, the module receives a privacy setting selection from the user and implements controls to comply with the selected privacy setting. In other embodiments, the module identifies data that is considered sensitive, encrypts data according to any appropriate and well-known method in the art, replaces sensitive data with codes to pseudonymize the data, and otherwise ensures compliance with selected privacy settings and data security requirements and regulations.

Persons skilled in the art will recognize that the devices, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An eye-mountable device, comprising:
   a flexible substrate having an eye-mounting surface configured to be positioned on an eye of a patient;

a resonant impedance sensor comprising an annular, flexible inductor loop concentric with a circumference of the flexible substrate and operable to obtain a measurement related to a condition of the eye of the patient at a time based on a change in the annular flexible inductor loop, wherein the resonant impedance sensor is coupled to the flexible substrate;

a therapeutic agent delivery assembly coupled to the flexible substrate; and a processor for executing a temporal model of a therapeutic agent delivery in communication with the sensor and the therapeutic agent delivery assembly, wherein the temporal model comprises a target measurement of the condition of the eye, wherein the processor is configured to:

receive the measurement related to the condition of the eye at the time from the resonant impedance sensor;

determine a measurement of the condition of the eye at the time based on a relationship between the measurement related to the condition of the eye at one time and the measurement of the condition of the eye at another time;

compare the measurement of the condition of the eye at the time to the target measurement of the condition;

determine an amount of a therapeutic agent to release from the therapeutic agent delivery assembly to the eye based on a difference between the measurement of the condition of the eye and the target measurement of the condition of the eye and the temporal model;

and activate the therapeutic agent delivery assembly to administer the amount of the therapeutic agent to the eye of the patient.

2. The device of claim 1, wherein the flexible substrate comprises a contact lens.

3. The device of claim 1, wherein the annular, flexible inductor loop has a variable diameter configured to increase or decrease based on an intraocular pressure change of the eye of the patient and is coupled to a capacitor to form a resonant circuit in communication with the processor, and wherein the processor is configured to receive resonance from the resonant circuit and to measure the intraocular pressure based on the resonance that is based on the variable diameter of the annular, flexible inductor loop.

4. The device of claim 3, wherein the resonant impedance sensor is configured to take multiple measurements spaced in time.

5. The device of claim 1, wherein the therapeutic agent delivery assembly comprises one or more therapeutic agent reservoirs and a thin film coupled to each of the one or more therapeutic agent reservoirs, and wherein the thin film is controlled by the processor and operable to open to release a therapeutic agent to the eye of the patient.

6. The device of claim 1, wherein the temporal model is based on a circadian rhythm of the patient.

7. The device of claim 6, wherein the temporal model is based on physiological data corresponding to the patient.

8. The device of claim 6, wherein the temporal model is generated and maintained by an adaptive neural network.

9. The device of claim 6, wherein the temporal model comprises a therapeutic agent delivery schedule.

10. The device of claim 1, wherein the resonant impedance sensor and the therapeutic agent delivery assembly are configured to operate in a closed loop.

11. A method for delivering a therapeutic agent to an eye of a patient, comprising:

receiving, by a processor coupled to an eye-mountable sensor, measurements related to a condition of the eye of the patient over a period of time from the eye-mountable sensor, wherein the eye mountable sensor comprises a flexible substrate and a resonant loop sensor having an annular, flexible inductor loop concentric with a circumference of the flexible substrate and having a diameter that changes based on the condition of the eye, wherein the measurements related to the condition of the eye are based on the diameter of the annular, flexible inductor loop;

establishing, by the processor, a temporal model for achieving a target measurement of the condition of the eye based on physiological characteristics of the patient, the patient's circadian rhythm, and the measurements related to the condition of the eye over the period of time;

receiving, by the processor, a measurement related to the condition of the eye at a time from the eye-mountable sensor;

determining, by the processor, a measurement of the condition of the eye at the time based on relationship between the measurement related to the condition of the eye at one time and the measurement of the condition of the eye at another time;

comparing, by the processor, the measurement of the condition of the eye at the time to a target measurement of the condition;

determining, by the processor, an amount of a therapeutic agent to release to the eye based on a difference between the measurement of the condition of the eye and the target measurement of the condition of the eye and the temporal model;

activating, by the processor, delivery of the amount of the therapeutic agent to the eye of the patent from a therapeutic agent delivery assembly coupled to the eye-mountable sensor; and modifying, by the processor, the temporal model based on the measurement of the condition of the eye at the time and measurements of the condition of the eye determined after the therapeutic agent is delivered.

12. The method of claim 11, wherein the measurements related to the condition of the eye of the patient are received as a resonant impedance of the annular, flexible inductor loop, wherein the resonant impedance is based on the diameter of the annular, flexible inductor loop that changes proportionally to the change in the condition of the eye being measured.

13. The method of claim 11, wherein activating delivery of the therapeutic agent to the eye of the patient comprises applying a voltage to a thin film disposed on a therapeutic agent reservoir of the therapeutic agent delivery assembly to open the thin film.

14. The method of claim 11, wherein the method is performed in a closed loop.

15. An eye-mountable device, comprising:

an intraocular pressure (IOP) sensor coupled to a contact lens, the IOP sensor comprising a resonant circuit comprising an annular, flexible inductor loop concentric with a circumference of the contact lens and having a diameter configured to change in response to a change in an IOP of the eye of the patient wearing the contact lens, wherein the change in the diameter of the annular, flexible inductor loop results in a change in the resonance of the resonant circuit, wherein the resonance change is reflective of the change in the IOP;

at least one reservoir coupled to the contact lens and comprising a therapeutic agent and a film positioned over an opening in the reservoir to seal the therapeutic agent within the reservoir; and a processor coupled to the contact lens and in communication with the IOP sensor and the at least one reservoir, wherein the processor comprises a temporal model configured to achieve a target IOP of the eye and is configured to:

receive the resonance of the resonant circuit of the IOP sensor at a time;

determine the IOP of the eye at the time based on the resonance of the resonant circuit of the IOP sensor at the time;

determine an amount of the therapeutic agent to release to the eye based on a comparison of the IOP of the eye at the time and the target IOP of the eye; and activate at least one of the at least one reservoir to release the amount of the therapeutic agent to the eye of the patient by applying a voltage to the film of the at least one reservoir, wherein the temporal model comprises time-dependent instructions for releasing the therapeutic agent to the eye of the patient, and wherein the processor activates the reservoir according to the temporal model.

16. The device of claim 15, wherein the temporal model is based on a circadian rhythm of the patient and the target IOP of the eye changes according to the circadian rhythm of the patient.

17. The device of claim 15, wherein the temporal model is based on physiological data corresponding to the patient and the target IOP of the eye is updated at intervals based on the physiological data corresponding to the patient.

18. The device of claim 15, wherein the IOP sensor and the reservoir are configured to operate in a closed loop.

19. The device of claim 15, wherein the temporal model is updated based on the determined IOP of the eye at the time over a plurality of time points.

* * * * *